(12) United States Patent
Sellinger et al.

(10) Patent No.: US 11,905,472 B2
(45) Date of Patent: Feb. 20, 2024

(54) ON-SITE SOLVENT GENERATION AND MAKEUP FOR TAR SOLVATION IN AN OLEFIN PLANT

(71) Applicant: Kellogg Brown & Root LLC, Houston, TX (US)

(72) Inventors: David Sellinger, Houston, TX (US); Rian Reyneke, Katy, TX (US); Alok Srivastava, Houston, TX (US); Kristine E. Hamilton, Houston, TX (US); Michael A. Radzicki, Houston, TX (US); Larry J. Shulik, Humble, TX (US); James R. Arnold, Highlands Ranch, CO (US); Quo-Chen Yeh, Sugar Land, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 17/729,963

(22) Filed: Apr. 26, 2022

(65) Prior Publication Data

US 2022/0340825 A1  Oct. 27, 2022

Related U.S. Application Data

(60) Provisional application No. 63/180,266, filed on Apr. 27, 2021.

(51) Int. Cl.
 *C10G 53/04* (2006.01)
(52) U.S. Cl.
 CPC ..... *C10G 53/04* (2013.01); *C10G 2300/1037* (2013.01); *C10G 2300/201* (2013.01); *C10G 2400/30* (2013.01)

(58) Field of Classification Search
 CPC ............ C10G 53/04; C10G 2300/1037; C10G 2300/201; C10G 2400/30
 See application file for complete search history.

(56) References Cited

U.S. PATENT DOCUMENTS 4,802,978 A   2/1989  Schmit et al.
4,831,200 A   5/1989  Debras et al.
(Continued)

FOREIGN PATENT DOCUMENTS

GB        907087 A   10/1962

OTHER PUBLICATIONS

Xu, R et al., "Cyclopentadiene Dimerization Kinetics in the Presence of C5 Alkenes and Alkadienes," pates 22516-22525, Industrial and Engineering Chemistry Research, vol. 58. Sep. 5, 2019; Entire Document; DOI: 10.1021/acs.iecr.9b04018.
(Continued)

*Primary Examiner* — Thuan D Dang
(74) *Attorney, Agent, or Firm* — Gary M. Machetta

(57) ABSTRACT

A system and process for generating, on-site, a sustained $C_6+C_7$ aromatic rich solvent stream for tar solvation within the olefin plant employing a two-fuel oil tower system receiving a hydrocarbon feed from a quench water separator drum, where the two-fuel oil tower system is configured to make a sufficient solvent stream containing $C_6+C_7$ aromatic rich hydrocarbons that is recycled and mixed with quench water going to the quench water separator drum to assist in removing tar molecules out of the quench water.

8 Claims, 2 Drawing Sheets

(56) References Cited

U.S. PATENT DOCUMENTS

| | | | |
|---|---|---|---|
| 4,997,543 A * | 3/1991 | Harandi | C10G 29/205 |
| | | | 208/66 |
| 5,090,977 A | 2/1992 | Strack et al. | |
| 5,877,363 A | 3/1999 | Gildert et al. | |
| 6,258,989 B1 | 7/2001 | Owen et al. | |
| 6,420,619 B1 | 7/2002 | Gartside et al. | |
| 6,576,132 B2 | 6/2003 | Kurukchi et al. | |
| 7,128,827 B2 | 10/2006 | Tallman et al. | |
| 7,294,749 B2 | 11/2007 | Verma et al. | |
| 7,527,725 B2 | 5/2009 | Viswanathan et al. | |
| 7,560,019 B2 | 7/2009 | McCoy et al. | |
| 7,741,526 B2 | 6/2010 | Kuechler et al. | |
| 8,025,773 B2 | 9/2011 | McCoy et al. | |
| 9,896,395 B2 | 2/2018 | Iaccino et al. | |
| 9,969,944 B2 | 5/2018 | Kurukchi et al. | |
| 10,619,112 B2 | 4/2020 | Al-Ghamdi | |
| 2002/0128528 A1 | 9/2002 | Pinault et al. | |
| 2006/0025641 A1 | 2/2006 | Gartside et al. | |
| 2007/0264176 A1 | 11/2007 | Stewart et al. | |
| 2008/0128323 A1 * | 6/2008 | McCoy | C10G 9/002 |
| | | | 208/69 |
| 2015/0175502 A1 | 6/2015 | Hwang et al. | |

OTHER PUBLICATIONS

Gao, S. et al., "The reaction kinetics of cyclopentadiene dimerizaiton using differential scanning calorimetry: Experiments and modelling" pp. 241-246, Thermochimica Acta. Vol. 589. Aug. 10, 2014; Entire Document; DOI: 10.1016/j.tca2014.05.031.

Yang, Z et al., "Molecular dynamics of the two-stage mechanism of cyclopentadiene dimerization: concerted or stepwise?" pp. 120-125. Chemical Physics. vol. 514. Oct. 25, 2018; Entire Document; DOI: 10.1016/j.chemphys.2018.02.020.

International Searching Authority, Patent Cooperation Treaty; International Application No. PCT/US2022/026535 filed Apr. 27, 2022; International Search Report and Written Opinion dated Jul. 29, 2022; 11 pages.

\* cited by examiner

ON-SITE SOLVENT GENERATION AND MAKEUP FOR TAR SOLVATION IN AN OLEFIN PLANT

CROSS REFERENCE TO RELATED APPLICATION

This application claims priority to U.S. Provisional Patent Application having Ser. No. 63/180,266 filed on Apr. 27, 2021 which is incorporated by reference herein.

TECHNICAL FIELD

The present invention relates to a system and a process for generating a $C_6+C_7$ aromatic rich solvent stream for tar solvation in a steam cracking olefin plant, such as an ethylene plant, and more particularly relates to a system and a process for generating a $C_6$-$C_7$ aromatic rich solvent stream for tar solvation that can tolerate disturbances in the hydrocarbon feed stream for the system and process.

BACKGROUND

Steam cracking, also referred to as pyrolysis, is a principal process used to produce lighter alkenes (e.g. ethylene), commonly known as olefins, from a naphtha, liquefied petroleum gas (LPG), ethane, propane, and/or butane feedstock.

In a conventional steam cracking process, a gaseous or liquid hydrocarbon feed like naphtha, LPG, or ethane is diluted with steam and briefly heated in a furnace without the presence of oxygen. The cracked gas products produced in the reaction depend on the composition of the feed, the hydrocarbon-to-steam ratio, and on the cracking temperature and furnace residence time. Light hydrocarbon feeds, such as ethane, LPGs, or light naphtha, give cracked gas streams rich in the lighter alkenes, including ethylene, propylene, and butadiene. Heavier hydrocarbons (full range and heavy naphthas as well as other refinery products) additionally yield products rich in aromatic hydrocarbons and hydrocarbons suitable for inclusion in gasoline or fuel oil, such as a $C_{5+}$ pyrolysis gasoline stream (i.e. pygas) leaving the bottom of a debutanizer tower used in the olefin plant for separating heavier hydrocarbons in the cracked gas stream from $C_4$ hydrocarbons. This pyrolysis gasoline stream usually contains $C_5$ diolefins and olefins, which can flash at elevated temperatures.

There are many parts of an olefin plant performing the multiple process steps required to produce the product gas and various by-products. For example, upon leaving the steam cracker unit, the cracked gas is sent to a quench system in which it is cooled with water. Ethane steam cracking systems, in particular, produce a cracked gas containing a small amount of molecules in the heavy fuel oil range ($C_{11+}$ range molecules) called tar. The density difference between tar and water in the quench water drum connecting to the quench tower used for cooling the cracked product gas is so small that it becomes very difficult to separate the very small quantity of tar from the water phase of the quench water. This results in circulating water carrying tar, which could foul the exchangers and the packings inside the quench tower.

A method called tar solvation has been employed to dissolve the tar and help separate it out of the water phase by introducing an external heavy aromatic stream containing heavy gasoline to fuel oil range molecules to the quench water drum. In these cases, the solvent used for tar solvation in ethane steam cracking systems is preferably an externally generated hydrotreated steam cracking pyrolysis gasoline that is introduced through a separate line to the quench water drum.

For example, U.S. Pat. Nos. 7,560,019 and 8,025,773 to ExxonMobil Chemical Patents Inc. disclose that in a system for thermal cracking gaseous feedstocks, where the system includes a gas cracker for producing an effluent comprising olefins, at least one transfer line exchanger for the recovery of process energy from the effluent and a water quench tower system, a process for extending the range of system feedstocks to include liquid feedstocks that yield tar is provided. The process includes the steps of injecting a first quench fluid downstream of the at least one transfer line exchanger to quench the process effluent comprising olefins, separating in a separation vessel a cracked product and a first byproduct stream comprising tar from the quenched effluent, directing the separated cracked product to the water quench tower system and quenching the separated cracked product with a second quench fluid to produce a cracked gas effluent for recovery and a second byproduct stream comprising tar into which an external aromatic rich stream is introduced to solvate the tar. An apparatus for cracking a liquid hydrocarbon feedstock that yields tar is also provided.

However, access to an external aromatic rich stream for tar solvation becomes difficult if there is no hydrotreating of pyrolysis gasoline unit on-site or if the location of the steam cracker is such that importing such a stream is infeasible or very expensive.

Thus, there is a need for generating, on-site, a suitable and sustainable aromatic rich solvent stream for dissolving the tar in the quench water to prevent it from fouling pipes, packing, and other equipment in the quench system of an olefin plant as the quench water is circulated to cool the cracked gas.

SUMMARY

There is provided, in one non-limiting embodiment, a system for generating on-site $C_6+C_7$ aromatic rich solvent stream including a quench water separator drum having sequential compartments including a last compartment, a primary fuel oil tower, and a secondary fuel oil tower where the quench water separator drum is connected to the primary fuel oil tower by a line directing a hydrocarbon stream from the last compartment of the quench water separator drum to the primary fuel oil tower, where there is a recycle line connecting an overhead stream of the primary fuel oil tower to a feed stream of the quench water separator drum, and where there is a line connecting a bottoms stream of the primary fuel oil tower to the secondary fuel oil tower. In an alternative embodiment, the system may further include a makeup stream connecting a portion of a $C_6+C_7$ rich bottoms stream of a debutanizer to the line directing a hydrocarbon stream from the last compartment of the quench water separator drum to the primary fuel tower. An alternative embodiment of the invention includes a system with a single fuel oil tower.

There is also provided, in different non-restrictive form, a process for generating on-site a $C_6+C_7$ aromatic rich solvent stream, where the process includes directing a hydrocarbon stream from a last compartment of a quench water separator drum to a primary fuel oil tower, separating $C_6+C_7$ aromatic hydrocarbons from $C_{8+}$ hydrocarbons in the primary fuel oil tower to form the $C_6+C_7$ aromatic rich solvent overhead stream and a $C_{8+}$ hydrocarbon bottoms stream, and recycling the $C_8+C_7$ aromatic rich solvent overhead stream to a feed stream of the quench water separator drum in an effective amount to separate tar from a water phase in the quench water separator drum and dissolve the tar in a hydrocarbon phase of the quench water separator drum.

Furthermore there is provided in another non-limiting embodiment an ethylene plant that includes a system for generating on-site a $C_6+C_7$ aromatic rich solvent stream, the system in turn including a quench water separator drum having sequential compartments including a last compartment, a primary fuel oil tower, and a secondary fuel oil tower where the quench water separator drum is connected to the primary fuel oil tower by a line directing a hydrocarbon stream from the last compartment of the quench water separator drum to the primary fuel oil tower, where there is a recycle line connecting an overhead stream of the primary fuel oil tower to a feed stream of the quench water separator drum, and where there is a line connecting a bottoms stream of the primary fuel oil tower to the secondary fuel oil tower. In an alternative embodiment, the system may further include a makeup stream connecting a portion of a $C_6+C_7$ rich bottoms stream of a debutanizer to the line directing a hydrocarbon stream from the last compartment of the quench water separator drum to the primary fuel tower.

DETAILED DESCRIPTION

It has been discovered that, in circumstances in which having access to an external aromatic rich stream for tar solvation is difficult or expensive, an indigenous, sustained $C_6+C_7$ aromatic rich solvent stream may be produced within the olefin plant by a two-fuel oil tower configuration (one primary fuel oil tower and one secondary fuel oil tower) designed to also make specification grade steam cracked naphtha (SCN) product ($C_5$-$C_{10}$ range molecules) and specification grade heavy fuel oil product ($C_{11+}$ range molecules) while also generating the desired solvent stream containing $C_6+C_7$ aromatic rich hydrocarbons that is mixed with quench water going to quench water separator drum to assist in removing tar molecules out of the quench water. In this two tower configuration, both the primary fuel oil separation tower and the secondary fuel oil separation tower operate at very low pressure to keep the operating temperature low, and so that steam is used as a stripping medium to control flash point in the fuel oil product. The desired stream containing $C_6$ and $C_7$ aromatic molecules are fractionated and produced intentionally, and this $C_6+C_7$ stream is mixed with quench water going to a quench water separator drum where it helps in removing tar molecules out of the water—thus achieving tar solvation. Directly addressing the presence of tar is important to manage fouling of exchangers and equipment in the quench system. Although it is a desirable goal to remove 100 wt % of the tar from the water, the process will be considered successful if at least 99.9 wt % of the tar is removed from the water, alternatively if at least 99.5 wt % of the tar is removed, and in another non-limiting embodiment 99.0 wt % of the tar is removed.

In other words, the amount of $C_6$ and $C_7$ aromatic molecules are made in small quantities from an ethane feed, in this process and system, the $C_6+C_7$ rich aromatic molecules are recycled in a closed loop. However, there will be at times loss of these molecules from the system due to equipment maintenance and draining. To avoid losing inventory of these desirable molecules, a makeup stream of debutanizer bottoms is provided to the primary fuel oil separation tower.

It has also been discovered that a $C_6+C_7$ aromatic rich solvent makeup stream may be generated by taking a portion of the bottoms stream of a debutanizer column located downstream in the olefin plant, which is comprised of $C_6+C_7$ aromatic rich hydrocarbons and is essentially free of $C_5$ hydrocarbons, after a $C_5$-rich side stream is drawn out of the debutanizer and providing the portion of the bottoms stream to the primary fuel oil tower to maintain inventory of $C_6+C_7$ aromatic rich tar solvation molecules in quench system. If some or all of this makeup stream is not used or if there is any surplus, the molecules are blended with pyrolysis gasoline product.

Figure 1:
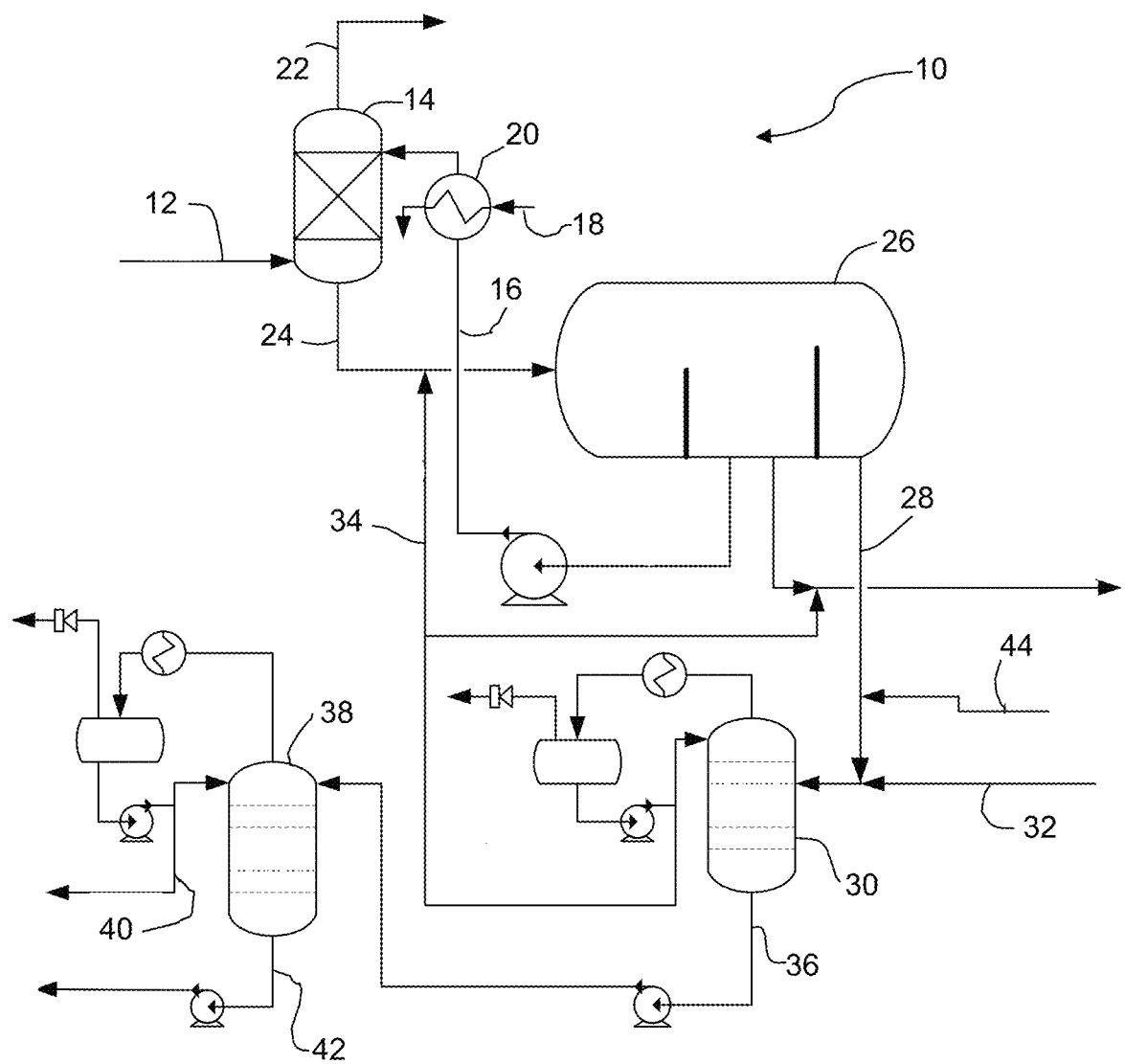
FIG. 1 is a schematic illustration of a non-limiting embodiment of a two-fuel oil tower system for producing a $C_6+C_7$ aromatic rich solvent stream for recycling to the quench water separator drum.

The schematic illustration in FIG. 1 shows one non-limiting embodiment of a system 10 and process for generating on-site a sustained $C_6+C_7$ aromatic rich solvent stream on the site of the olefin plant where the system 10 resides. More specifically referring to FIG. 1, process gas 12 from the pyrolysis furnaces (not shown), in a non-limiting embodiment at about 450° F. (about 232° C.) is fed to quench tower 14 where the process gas 12 is further cooled by direct contact with quench water 16. Typical quench tower tar limits without tar solvation are about 1 wt %, typical of butane cracking, in the process gas feed to the tower 14. Tar solvation dramatically improves the quench water quality also for feedstocks that make <1 wt % tar, like ethane and propane. Quench water 16 may be cooled against cooling water 18 (CW) in heat exchanger 20. For sites that recycle dilution steam (not shown), the water may be sent to the steam generators. Advantageously, in such cases, the tar solvation greatly reduces steam generator fouling. Benefits may also be realized for gas cracker systems that do not recycle steam. Due to the use of tar solvation, the water leaving quench water separator drum 26 should be clear and clean, and thus avoids downstream or later fouling of the quench circuit typically attributable to tar. Tar solvation turns the quench water separator drum 26 from a three phase separator with tar on the bottom, to a two phase separator with tar in the top light hydrocarbon phase.

Quench Tower Overhead vapor 22 is sent to a process gas compressor (PGC; not shown), in one non-limiting embodiment at a temperature of about 100° F. (about 38° C.), whereas the quench tower bottoms stream 24 containing condensed hydrocarbons is fed to quench water separator drum 26, which has a plurality of compartments. A hydrocarbon phase stream 28 from the last compartment of quench water separator drum 26 is sent to the primary fuel oil separation tower 30. Hydrocarbons 32 condensed in the process gas compressor (PGC; not shown) second stage may be also combined with hydrocarbon feed 28 from the quench tower separator drum 26.

The primary fuel oil separation tower 30 separates $C_6+C_7$ aromatic rich hydrocarbons in an overhead stream 34 from a $C_{8+}$ hydrocarbon bottoms stream 36 through fractionation. Upon separation, the $C_6+C_7$ aromatic rich hydrocarbons in an overhead stream 34 from the primary fuel oil separation tower 30 overhead is recycled back to the quench tower bottoms feed 24 to create an effective concentration of C$_6$+C$_7$ aromatics in the quench water separator drum 26 to keep tar dissolved in hydrocarbon phase. The lower density of C$_6$+C$_7$ aromatic rich solvent overhead stream 34 helps in separating the water phase of the quench water in the quench water separator drum 26 from the hydrocarbon phase stream 28.

It will be appreciated that the primary fuel oil separation tower 30 is operated at low pressure to keep operating temperature low and steam is injected to lower the boiling point of the tower bottoms. Non-limiting examples of the pressure that may be used ranges from about 12 psia (83 kPa) independently to about 17 psia (117 kPa); alternatively from about 15 psia (103 kPa) independently to about 17 psia (117 kPa). When the term "independently" is used herein with respect to a range, it is meant that any threshold maybe used together with any other threshold given to provide a suitable alternative parameter range. Non-limiting examples of the operating temperature that may be used ranges from about 180° F. (82° C.) independently to about 320° F. (160° C.); alternatively from about 200° F. (93° C.) independently to about 280° F. (138° C.).

Referring again to the non-limiting embodiment shown in FIG. 1, the C$_{8+}$ hydrocarbon bottoms stream 36 of the primary fuel oil separation tower 30 is fed to a secondary fuel oil separation tower 38 (running under deep vacuum for the reasons above) to produce a C$_8$-C$_{10}$ steam cracked naphtha (SCN) stream 40 and a C$_{11+}$ heavy fuel oil product stream 42. In more detail, the secondary fuel oil separation tower 38 may be operated at a pressure in the range of from about 2 psia (14 kPa) independently to about 7 psia (48 kPa); alternatively from about 2 psia (14 kPa) independently to about 4 psia (28 kPa), and at an operating temperature that may be used ranges from about 200° F. (93° C.) independently to about 280° F. (138° C.).

It is further appreciated that, despite being produced and recycled in a closed loop as shown in FIG. 1, since C$_6$+C$_7$ aromatic molecules may originate only in small quantities from the ethane stream cracker furnace in the plant, upsets in the system 10 described herein due to pump draining and equipment maintenance may lead to problems with the material balance in the system 10 and losses of C$_6$+C$_7$ molecules. To avoid a loss in on-site supply of these molecules, a C$_6$-C$_7$ rich tar solvent makeup stream 44 of C$_6$+C$_7$ may be generated from a debutanizer column 48 that is further downstream of the quench and two-fuel oil tower systems in the olefin plant.

Figure 2:
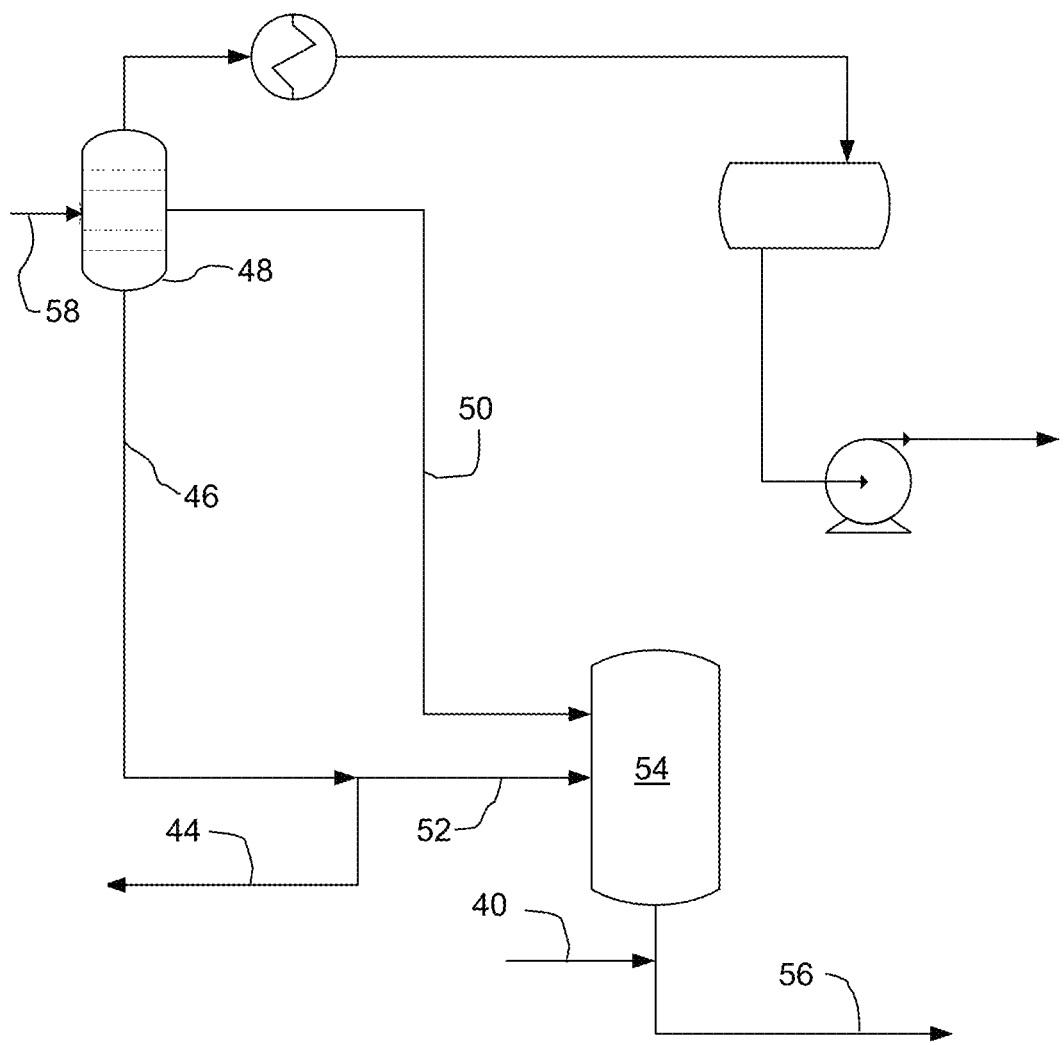
FIG. 2 is a schematic illustration of a non-limiting embodiment of a debutanizer system with a $C_5$-rich side draw stream for production of a $C_5$-free and $C_6+C_7$ rich bottoms stream for use as a tar solvent makeup for a quench water separator drum.

More specifically, a C$_6$+C$_7$ makeup stream 44 may be generated by, in the embodiment illustrated in FIG. 2, taking a portion of the C$_6$-C$_7$ rich bottoms stream 46 of a debutanizer column 48 receiving hydrocarbon feed 58 located downstream in the olefin plant, which is comprised of C$_6$+C$_7$ aromatic rich hydrocarbons and is essentially free of C$_5$ hydrocarbons (which are not understood to be useful for dissolving tar at the quench water separator drum 26 operating temperature), after a C$_5$-rich side draw stream 50 is drawn out of the debutanizer column 48 and providing the portion of the C$_6$-C$_7$ rich bottoms stream 46 to the primary fuel oil separation tower 30 as C$_6$-C$_7$ rich tar solvent makeup stream 44.

Referring again to the non-limiting embodiment of the system and process shown in FIG. 2, the debutanizer column 48 is configured to produce a C$_5$-rich side draw stream 50. The operating conditions of the debutanizer column 48 include an overhead pressure of from about 29 psia (200 kPa) independently to about 130 psia (896 kPa) depending on condensing media (i.e., refrigerant, cooling water) and an overhead operating temperature ranging from about 1° F. (−17° C.) independently to about 113° F. (45° C.); and a bottoms temperature from about 180° F. (82° C.) independently to about 280° F. (138° C.). It will be appreciated that the location of C$_5$-rich side draw 50 should be carefully evaluated through simulation of the debutanizer column 48 to ensure that the C$_5$-rich side draw 50 has the highest concentration of C$_5$ range hydrocarbons in order to minimize the amount of C$_5$ range hydrocarbons concentration in C$_6$-C$_7$ rich bottoms stream 46 of debutanizer column 48. In accordance with this non-limiting embodiment, the C$_6$-C$_7$ rich bottoms stream 46 of debutanizer column 48 mainly consists of C$_6$+C$_7$ range hydrocarbons, a portion of which, based on the C$_6$-C$_7$ rich tar solvent makeup stream 44 needs of the two-fuel oil tower system and process shown in FIG. 1, is withdrawn as suitable C$_6$-C$_7$ rich tar solvent makeup stream 44 for tar solvation.

After drawing the necessary C$_6$-C$_7$ rich tar solvent makeup stream 44 for the quench system, net debutanizer bottoms stream 52 may be mixed with C$_5$-rich side draw stream 50 in a pyrolysis gasoline drum 54 as net pyrolysis gasoline 56.

In the absence of an external source of aromatic rich solvent, such as is required in U.S. Pat. Nos. 7,560,019 and 8,025,773, the above-described system and process provides a distinct advantage over past invention to conduct tar solvation and avoid potential fouling of heat exchanges, quench tower packings, and other equipment.

In the foregoing specification, the invention has been described with reference to specific embodiments thereof. However, the specification is to be regarded in an illustrative rather than a restrictive sense. For example, fuel oil separation tower conditions and configurations, quench system conditions and configuration, debutanizer conditions and configuration, and the composition and amount of the various hydrocarbon and water streams falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. In a non-limiting embodiment, there may be provided a system for generating on-site a C$_6$+C$_7$ aromatic rich solvent stream, where the system comprises, consists essentially of, or consists of a quench water separator drum having sequential compartments including a last compartment, a primary fuel oil separation tower, and a secondary fuel oil separation tower; where the quench water separator drum is connected to the primary fuel oil separation tower by a line directing a hydrocarbon stream from the last compartment of the quench water separator drum to the primary fuel oil separation tower, there is a recycle line connecting an overhead stream of the primary fuel oil separation tower to a feed stream of the quench water separator drum; and there is a line connecting a bottoms stream of the primary fuel oil separation tower to the secondary fuel oil separation tower.

There may be also provided in another non-restrictive version a process for generating on-site a C$_6$+C$_7$ aromatic rich solvent stream, where the process comprises, consists essentially of, or consists of directing a hydrocarbon stream from a last compartment of a quench water separator drum to a primary fuel oil separation tower, separating C$_6$+C$_7$ aromatic hydrocarbons from C$_{8+}$ hydrocarbons in the primary fuel oil separation tower to form the C$_6$+C$_7$ aromatic rich solvent overhead stream and a C$_{8+}$ hydrocarbon bottoms stream, and recycling the C$_6$+C$_7$ aromatic rich solvent overhead stream to a feed stream of the quench water separator drum in an effective amount to separate tar from a water phase in the quench water separator drum and dissolve the tar in a hydrocarbon phase of the quench water separator drum.

There may be further provided in a different non-limiting embodiment an ethylene plant comprising a system for generating on-site a $C_6+C_7$ aromatic rich solvent stream, where the system comprises, consists essentially of, or consists of a quench water separator drum having sequential compartments including a last compartment, a primary fuel oil separation tower, and a secondary fuel oil separation tower; where the quench water separator drum is connected to the primary fuel oil separation tower by a line directing a hydrocarbon stream from the last compartment of the quench water separator drum to the primary fuel oil separation tower, there is a recycle line connecting an overhead stream of the primary fuel oil separation tower to a feed stream of the quench water separator drum; and there is a line connecting a bottoms stream of the primary fuel oil separation tower to the secondary fuel oil separation tower.

The words "comprising" and "comprises" as used throughout the claims, are to be interpreted to mean "including but not limited to" and "includes but not limited to", respectively.

To the extent used herein, the word "substantially" shall mean "being largely but not wholly that which is specified."

As used herein, the singular forms "a," "an," and "the" are intended to include the plural forms as well, unless the context clearly indicates otherwise.

To the extent used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

What is claimed is:

1. A system for generating on-site a $C_6+C_7$ aromatic rich solvent stream, the system comprising:
    a quench water separator drum having sequential compartments including a last compartment;
    a primary fuel oil separation tower;
    a secondary fuel oil separation tower;
    a first line connecting the quench water separator drum to the primary fuel oil separation tower and configured to direct a hydrocarbon stream from the last compartment of the quench water separator drum to the primary fuel oil separation tower;
    a makeup stream comprising a portion of a $C_6+C_7$ aromatic hydrocarbons rich bottoms stream essentially free of $C_5$ hydrocarbon of a debutanizer receiving a hydrocarbon feed located downstream of an olefin plant, wherein the debutanizer is connected to the first line, and wherein the debutanizer comprises a $C_5$ hydrocarbon rich side draw stream;
    a recycle line connecting an overhead stream of the primary fuel oil separation tower to a feed stream of the quench water separator drum; and
    a second line connecting a bottoms stream of the primary fuel oil separation tower to the secondary fuel oil separation tower.

2. The system of claim 1, further comprising a quench tower comprising a quench tower overhead stream and a quench tower bottoms stream, wherein the quench tower bottoms stream is fed to the quench water separator drum.

3. The system of claim 1, wherein the quench water separator drum comprises a two-phase separator having tar in a top light hydrocarbon phase.

4. The system of claim 1, wherein tar present in the feed stream to the quench water separator drum is dissolved in a hydrocarbon phase in the quench water separator drum.

5. An ethylene plant comprising:
    a system for generating on-site a $C_6+C_7$ aromatic rich solvent stream, the system comprising:
        a quench water separator drum having sequential compartments including a last compartment;
        a primary fuel oil separation tower; and
        a secondary fuel oil separation tower;
    a first line connecting the quench water separator drum to the primary fuel oil separation tower and configured to direct a hydrocarbon stream from the last compartment of the quench water separator drum to the primary fuel oil separation tower;
    a makeup stream comprising a portion of a $C_6+C_7$ aromatic hydrocarbons rich bottoms stream essentially free of $C_5$ hydrocarbon of a debutanizer receiving a hydrocarbon feed located downstream of an olefin plant, wherein the debutanizer is connected to the first line, and wherein the debutanizer comprises a $C_5$ hydrocarbon rich side draw stream;
    a recycle line connecting an overhead stream of the primary fuel oil separation tower to a feed stream of the quench water separator drum; and
    a second line connecting a bottoms stream of the primary fuel oil separation tower to the secondary fuel oil separation tower.

6. The ethylene plant of claim 5, further comprising a quench tower comprising a quench tower overhead stream and a quench tower bottoms stream, wherein the quench tower bottoms stream is fed to the quench water separator drum.

7. The ethylene plant of claim 5, wherein the quench water separator drum is a two-phase separator having tar in a top light hydrocarbon phase.

8. The ethylene plant of claim 5, wherein tar present in the feed stream of the quench water separator drum is dissolved in a hydrocarbon phase in the quench water separator drum.

* * * * *